United States Patent [19]

Aslanian et al.

[11] Patent Number: 5,240,035
[45] Date of Patent: Aug. 31, 1993

[54] PRESSURE COMPENSATED FLOW CONTROL DEVICE FOR IV ADMINISTRATION

[75] Inventors: Jerry L. Aslanian, Paradise Valley, Ariz.; Robert J. Wright, Newport Beach, Calif.

[73] Assignee: Jerry Aslanian, Scottsdale, Ariz.

[21] Appl. No.: 664,357

[22] Filed: Mar. 4, 1991

[51] Int. Cl.$^5$ .............................................. G05D 7/01
[52] U.S. Cl. ................................... 137/501; 604/247
[58] Field of Search .......................... 137/501; 604/247

[56] References Cited

U.S. PATENT DOCUMENTS

| | | |
|---|---|---|
| 4,043,332 | 8/1977 | Metcalf. |
| 4,343,305 | 8/1982 | Bron .............................. 137/501 X |
| 4,515,588 | 5/1985 | Amendolia ..................... 604/247 X |
| 4,769,012 | 9/1988 | Quang ................................. 604/247 |
| 4,998,556 | 3/1991 | Bron .................................... 137/501 |

*Primary Examiner*—Robert G. Nilson
*Attorney, Agent, or Firm*—Gregory J. Nelson

[57] ABSTRACT

A pressure compensator for maintaining essentially constant flow rates in an IV system having a source of IV fluid and a controller. The compensator is connectable to the controller and has a housing with a flexible membrane extending transversely therein defining opposite control chambers. One control chamber communicates with the source of IV fluid and also connects the inlet of the flow controller. The second control chamber receives the regulated flow from the control valve. The second control chamber is generally conical or convex sloping to an outlet port which is connected to the tubing line leading to the patient. The outlet from the second chamber is smaller than the inlet to the second chamber and the diaphragm serves to control the flow to the patient compensating for pressure changes such as a change in fluid head. The configuration of the second chamber and the configuratoin of the outlet in the second chamber minimize air entrapment and provide greater flow capacity.

13 Claims, 2 Drawing Sheets

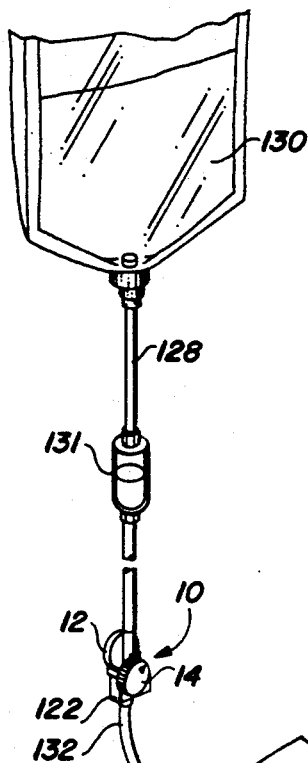
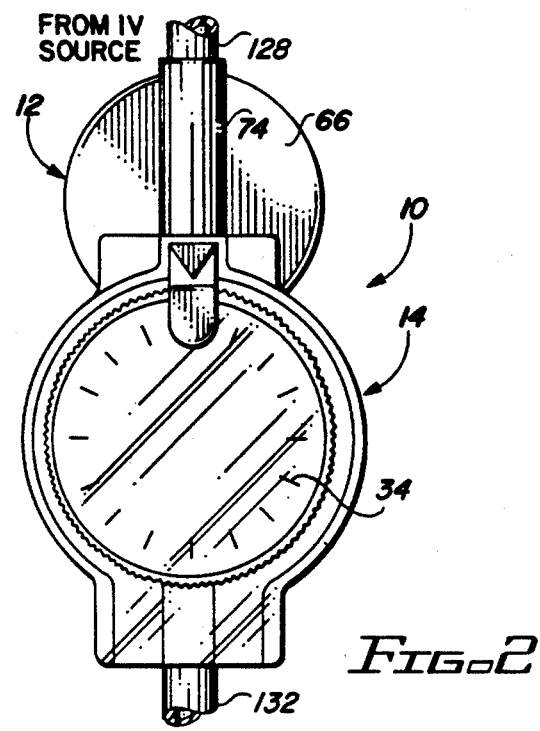
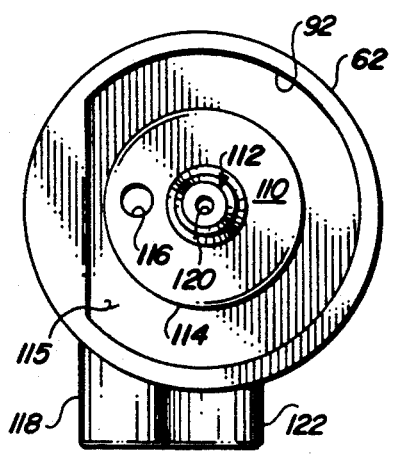
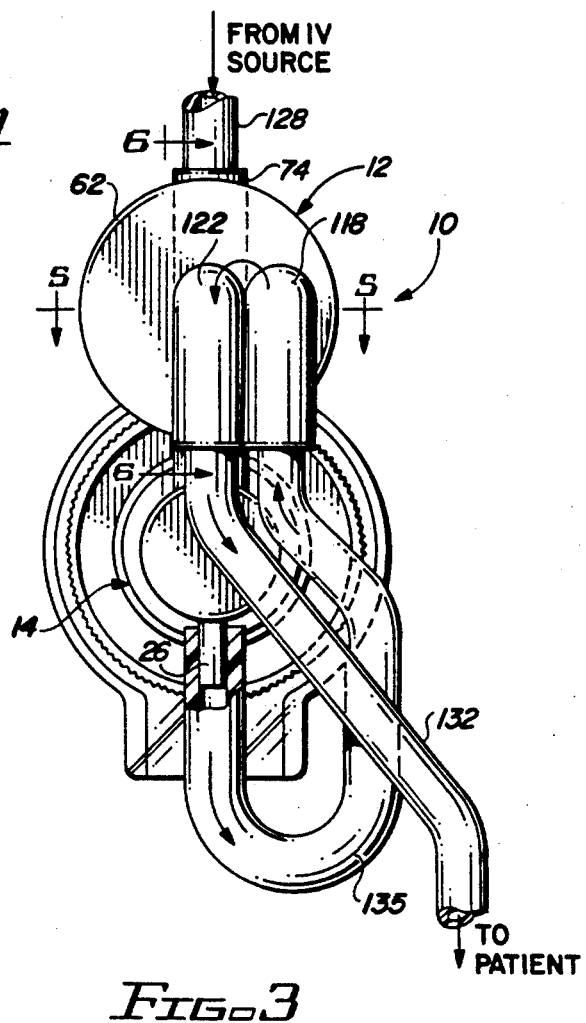

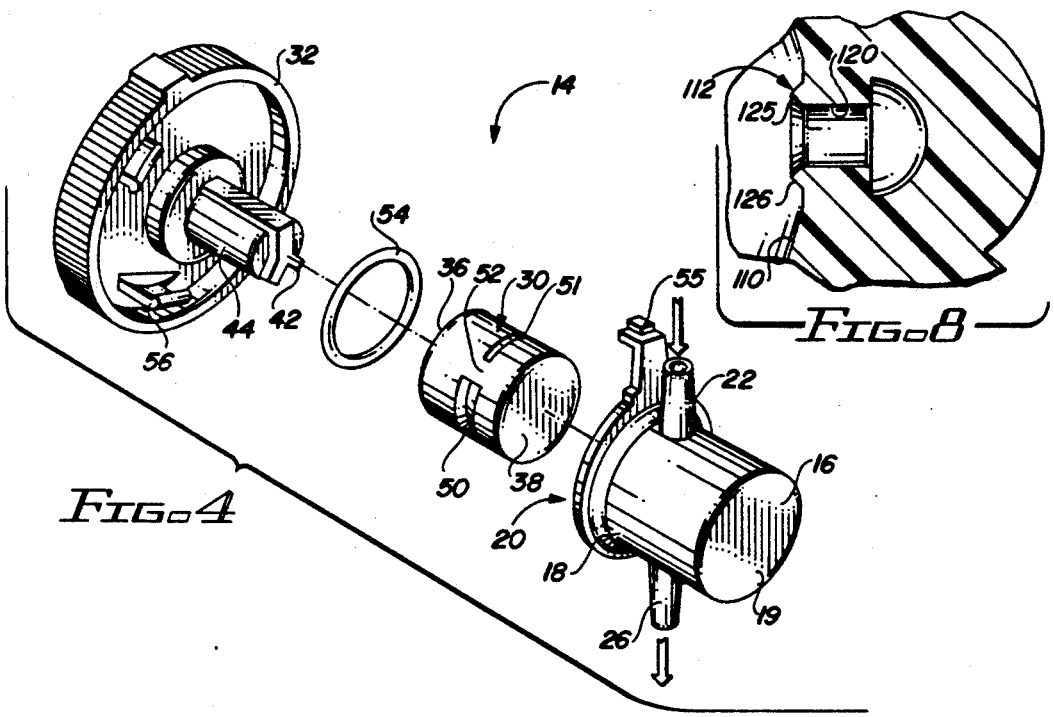
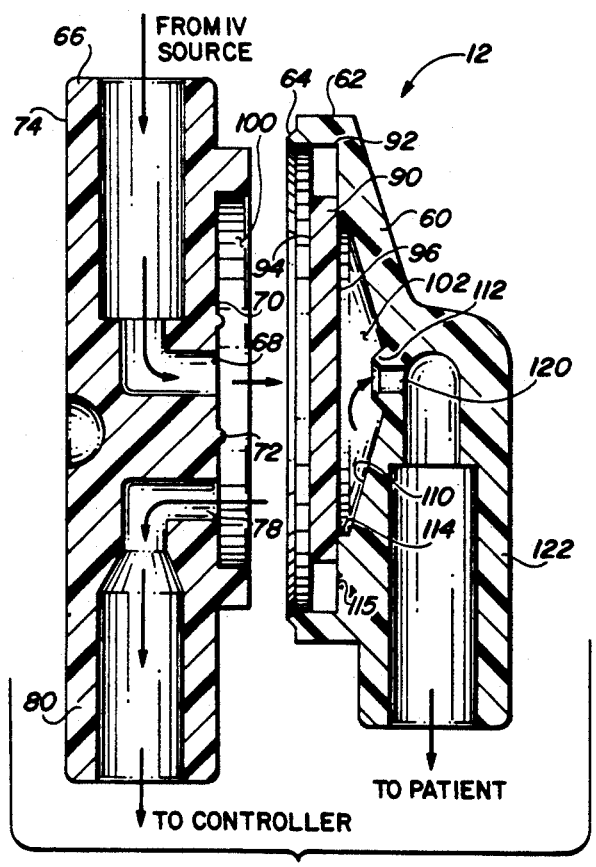
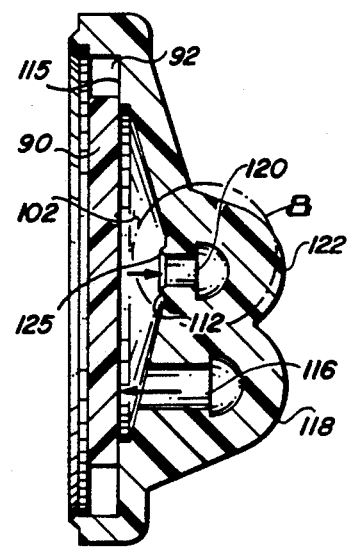

PRESSURE COMPENSATED FLOW CONTROL DEVICE FOR IV ADMINISTRATION

The present invention relates to a device for regulating and controlling the flow of intravenous (IV) solutions to a patient and more particularly relates to a disposable flow regulation device which is adjustable to establish a predetermined rate of flow and which device will maintain said predetermined flow irrespective of changes in the elevation of the IV fluid level and/or changes in the location of the administration or venous puncture site.

Gravity administration of fluids by IV infusion is a common medical procedure. Representative intravenous fluids include blood, plasma, dextrose, glucose and isotonic saline solutions.

Typically IV containers have a seal which is broken by the insertion of a spike and the fluid is deliver to the patient at an administration needle through a drip chamber via flexible tubing connected to the spike. The purpose of the drip chamber is to facilitate the determination of the flow or drip rate through the tubing. Infusion rates may be regulated by use of an external pinch valve or roller clamp associated with the tubing for more common, non-critical, gravity-type infusions.

Initially when the infusions are carried out, the tubing and needle are purged of air by initiating a flow of fluid through the tubing. The needle is then inserted into a venous puncture site on the patient such as in the forearm or wrist and fluid flow begun. When the venous puncture site is located in the lower arm of the patient, the arm should be properly stabilized, preferably using a contoured IV arm arm support. Medical personnel administering the IV support will adjust the pinch valve or roller clamp to restrict the IV tubing and the number of drops passing through the drip chamber are visually counted. The appropriate flow rate is established by trial and error by progressively restricting or opening the tubing pinch valve. The administration procedure described above requires the attention of medical personnel for a substantial period of time.

More sophisticated gravity control systems have replaced the pinch valve or roller clamp in many applications providing accurate flow metering. For example, U.S. Pat. Nos. 4,294,246 and 4,361,147 disclose devices which represent substantial improvements over prior art pinch valves and roller clamps. The devices shown in these patents have a flow passage within a housing which is connectable to a source of IV fluid and to a delivery tube terminating at an administration needle. Precise metering is accomplished by a metering pin axially moveable within the flow passage relative to a valve seat which defines a flow passageway and variable area flow notch which are positionable relative to the valve seat to regulate flow from a full flow purge position to a flow blocking position. In the preferred embodiment, the positioning of the metering pin is accomplished by a cam engaging a portion of the metering pin which forms a cam follower. The cam is manually adjustable by a dial on the device to accomplish accurate, repeatable, and continuous flow adjustment over a flow range. The system incorporates a metering apparatus, a source of IV fluid, a drip chamber and administration means. The controller and system of these patents has achieved acceptance in the medical community under the designation "IV Master Flow".

Other patents such as U.S. Pat. No. 4,789,000 disclose further improvements in IV metering devices. This patent discloses a metering apparatus and system for controlling the administration of IV fluids having a valve housing with an inlet and outlet and having a rotatable valving member positioned in the body. A valve passageway of variable cross sectional area is provided in the valving member. The effective area and length of the valve passageway interposed between the inlet and outlet of the valve is rotatably adjustable to regulate flow by rotating the valve body relative to the valve member. This device is sold by Master Medical Corporation under the trademark "Stat 2".

While controllers as shown in the aforementioned patents represent substantial improvements over the prior art in providing low-cost, efficient, repeatable and highly accurate flow settings, certain variable conditions in the IV administration procedure may nevertheless cause the rate of flow to change after the valve has been set regardless of the inherent accuracy and effectiveness of the controller valve. The flow rate in an IV administration set is basically a function of the fluid head in the system, that is, the differential height between the venous puncture site and the effective level of the IV fluid. If, for example, a medical attendant changes the position of the IV fluid supply on the stand, the flow rate will be affected. Similarly, if the patient raises or lowers an arm and changes the height of the venous puncture site, flow rates may be similarly effected. Another variable which affects head height and alters flow rates is the gradual lowering of the liquid supply within the IV container in the administration procedure. It is obviously not possible for a medical attendant to be continually present to monitor the patient and make any necessary changes in the setting of the IV control valve and thus flow rate changes normally occur to some extent. In non-critical situations, some flow rate change is tolerated but in some situations, precise flow rate control must be maintained.

Various expedients have been resorted to in an effort to maintain constant IV flow rates in gravity systems. U.S. Pat. No. 4,343,305 discloses an adjustable rate, constant output infusion set having a connector piece connectable to a container and a head piece rotatably attached to the connector to adjust the flow rate. An elastically stretchable diaphragm is interposed between the connector piece and the head piece. The connector piece forms a first chamber with the diaphragm which is in direct communication with the container via an inlet port. The head piece forms a second chamber with the diaphragm which is in communication with the patient via a control port. The head piece is rotatably attached to the connector to adjust the flow rate. A passageway connects the first chamber and the second chamber and the diaphragm, by virtue of its elasticity, maintains a constant pressure drop between the chambers so that liquid passes the control port at a constant rate of flow.

U.S. Pat. No. 4,515,588 shows a flow regulator for use in an IV administration arrangement which establishes and maintains the rate of liquid flow regardless of changes of the head. The regulator utilizes a diaphragm-controlled orifice and a bypass with a valve to establish the flow rate. The diaphragm adjusts the effective orifice opening to maintain constant the flow selected by the valve.

U.S. Pat. No. 4,769,012 discloses a flow regulating device for gravity infusion and transfusion of fluids which has an upper and lower housing having inlet and outlet channels respectively. A continuously adjustable valve is connected between the in-flow and out-flow channels. The out-flow channel has an outlet opening which defines a valve seat and a membrane extends across the outlet opening and is moveable toward and away from the outlet opening depending on pressure occurring on opposite sides of the membrane. In this way, extraneous factors such as patient venous pressure can be compensated for by the membrane to maintain a substantially constant flow of fluid once the valve is set.

While the devices described above provide some improved accuracy in IV deliveries, they may not be economically justifiable in some applications. Further, the devices are internally complex making them expensive to manufacture and subject to internal leakage. Accordingly, there exists a need for a reliable, accurate, inexpensive and effective pressure compensator device for use with IV controllers to maintain a substantially constant flow of IV fluid once the valve is set which compensator is economical and may be used as an adjunct to or in combination with flow control devices.

Briefly, the present invention achieves the above objects and advantages and provides a unique IV control and pressure compensator device for gravity systems which can be adjusted to maintain various IV settings from zero to full-flow with accuracy and repeatability and which will maintain a substantially constant flow of fluid at the valve setting once the valving is set regardless of changes in head pressure occurring in the IV administration set.

In accordance with a preferred embodiment of the present invention, a pressure compensator device is provided in combination with a flow control device. The flow control device has a housing with an inlet and outlet. A flow metering member having a variable area flow passage is adjustable within the housing by means of a manually adjustable dial. The flow metering member selectively places the inlet and outlet ports of the flow control member in communication via the flow passage to regulate the flow from a purge position, through a flow adjusting range, to a flow stop or blocking position. The compensator unit is adapted to be connected to the flow control device in a piggy-back manner. The flow compensator has a housing which is divided into opposed first and second pressure control chambers by a transversely extending flexible diaphragm. The first pressure chamber is connected to the source of IV fluid at an inlet fitting. An outlet from the first chamber connects to the inlet of the flow control device. The controlled output flow of the flow control device is redirected to the second chamber, preferably at a location displaced from the center of the chamber. The second control chamber is specially configured to permit substantial flow at high settings when rapid infusions are required and also to provide precise control eliminating air entrapment which is a common disadvantage of prior art compensation devices. An outlet from the second pressure chamber extends from the proximate center of the second chamber and is connectable to flexible tubing which connects to an administration needle at the patient. The diaphragm is responsive to changes in head pressure, as for example, changes in the height of the fluid level or venous pressure to restrict the control of flow from the flow control member to the patient. An increase in patient's venous pressure can be compensated for by the reduction of the throttling effect or restriction occurring at the outlet from the second control chamber. Similarly, a decrease in head pressure will similarly be automatically compensated for by reduction of the throttling effect through the compensator.

The above and other objects and advantages of the present invention will become more apparent from the following description, claims and drawings in which:

FIG. 1 illustrates a typical IV system with the compensated controller connected in the system;

FIG. 2 is a front view of the compensator and controller;

FIG. 3 is a rear view of the compensator and controller;

FIG. 4 is an exploded view of the controller;

FIG. 5 is a sectional view taken along line 5—5 of FIG. 3;

FIG. 6 is a sectional view taken along line 6—6 of FIG. 3;

FIG. 7 is a front view of the controller with the cover removed illustrating the second control chamber; and FIG. 8 is a detail of the outlet of the second pressure control chamber.

Turning now to the drawings, FIGS. 1 to 8 generally show an embodiment of the compensated flow control device of the present invention which is designated by the numeral 10. The compensated flow control device 10 includes a compensator portion 12 and a flow controller 14 which are of the gravity-flow type and preferably disposable, single-use devices. The flow controller 14, as best seen in FIG. 4, includes a generally cylindrical housing 16 which has a side wall 18 and an end wall 19 defining an internal valve chamber 20. Fitting 22 defines an inlet port which communicates with the valve chamber 20. Fitting 26 is oppositely disposed from fitting 22 and defines an outlet port. The inlet and outlet are connectable to tubing lines 128 and 132, respectively.

A valving member 30 is rotatively received within the valve chamber 20. The rotary valving member has a knurled dial 32 to facilitate manual rotation of the valving member and adjustment of the controller. The dial 32 carries appropriate indicia 34 which cooperate with pointer 55 to provide an indication of the flow rate setting. Dial 32 is attached to a projection 44 which is received within the member 30.

The valving member 30 has a generally cylindrical body having an open upper end 36 and a closed bottom end 38. The closed end 38 is configured having a recess therein conforming to the general Y-configuration of end 42 of projection 44. Thus, when the valving member 30 is placed over the projection 44 and the components forced together, end 42 will seat in valving member 30 to ensure proper alignment and to prevent relative rotation between these components.

Preferably the valve housing 16 is fabricated from a rigid, hard plastic such as ABS or the like which is medically acceptable, will resist deformation and deflection, and may be bonded by solvents. One particularly suitable material is the type of ABS sold under the trade name "Kadon". Similarly, the rotative valve assembly consisting of projection 44 and the manual dial 32 is preferably fabricated from rigid hard plastic. The valving member 30 is preferably fabricated from a relatively softer, semi-rigid material such as PVC, LDP, C-Flex or other similar medically acceptable plastic materials known to those in the art which will accommodate tolerance variations and will maintain a proper seal with the rigid material of the body.

The valving or flow control function is accomodated by means of a flow channel 50 and variable area metering groove 51 formed in the outer surface of the valving member. The flow channel is generally U-shaped or V-shaped in cross section and communicates at one end with the metering groove which extends part way around the drum leaving a land area 52. The metering groove 51 is of varying cross-sectional area decreasing from a maximum at the point of intersection with the flow channel.

In operation, the flow controller 14 is in the full open or purge position when a portion of the flow channel 50 is aligned with the inlet 22 and the opposite end of the flow channel is aligned with the outlet 26. In this position, fluid will flow through the inlet port and along the flow channel to the outlet port to provide a full flow and flow purging condition which, for example, would be used to initially purge the system of air when IV procedures are begun.

When the valving member is rotated to a flow metering position, IV fluid will flow from the inlet through the passageway defined by a portion of the channel 50 and a portion of the metering groove 51 to the outlet 26. As the valve member 30 is further rotated, a longer circumferential portion or flow path of the metering groove 51 is placed in the flow path to achieve metering of flow. When the valve member is rotated to a position in which the land 52 is in registry with the inlet, the valve is in a flow blocking or "off" position.

The above is representative of one of a number of possible valving configurations which may be incorporated to meter and control flow using a flow controller. Other configurations, for example, may be found in U.S. Pat. No. 4,802,506 in which flow passageway is extended by means of a parallel flow passage so as to extend the flow control range to approximately a full 360° of the drum surface.

The flow controller may include an O-ring 54 about the inner end of the valving member which is received in an annular seat in the valve body. The components including the valve housing, valving member and dial may be snapped together with the flanges 56 on the underside of the dial engaging the external lip about the opening in the valve body. As indicated above, the surface of the dial may be provided with appropriate indicia 34 for indicating various flow settings. The indicia cooperate with a reference marker 55 formed as an integral part of the valve body.

The description of the flow controller 14 set forth above is to facilitate an understanding of the present invention and to provide a representative operating environment. Other types of gravity flow controllers will also work well with the compensator of the present invention as, for example, the controller of U.S. Pat. Nos. 4,294,246 and 4,361,147 which description is incorporated by reference herein. One particular advantage of the compensator of the present invention is that it may be utilized as an accessory or add-on component to IV flow controllers of various constructions.

The novel flow compensator is designated by the numeral 12 and includes a housing 60 having a generally circular wall 62. An annular flange 64 extends around the upper edge of the wall 62 which receives a cover plate 66. The cover plate 66 defines a central port 68 extending to the inner surface 70. A small annular flange 72 extends around the port 68 at surface 70 which serves the function of a check valve. The check valve function will prevent back flow which may be important in a lower Y-site connection for addition of other fluids in the system. Infiltration of debris such as undissolved solids and foreign particulates of plastic or other material is also reduced by the addition of the check valve. An in-line filter may be inserted upstream of the unit to further reduce infiltration of debris. As will be explained, a flexible diaphragm 90 cooperates with the flange 72 to maintain a seal until pressure is introduced into the system as the uncaptured diaphragm is held against the annular flange 72 until fluid pressure is present.

Inlet port 68 communicates with fitting 74 on the exterior of plate 66. Outlet port 78 extends to surface 70 radially spaced-apart from inlet port 68 and communicates with fitting 80 which is connected by flexible tubing to the controller 14. Plate 66 and housing 60 are injection molded from a medically-acceptable plastic such as ABS or XT and are secured together as a unitary structure by welding, adhesives or similar joining techniques.

A generally circular, flexible diaphragm 90 is freely supported. The diaphragm is preferably formed of a flexible medically acceptable material such as silicon rubber and has a generally disk-like configuration with opposite planar parallel surfaces 94, 96. The location and thickness of the diaphragm is selected with respect to the depth of shoulder 92 so the diaphragm is not "captured" and accordingly diaphragm 90 is allowed limited freedom of movement even at its periphery with respect to surfaces 70 and 115. For example the thickness of the diaphragm at rest should be selected to provide at least 0.002" clearance with the opposite housing surfaces.

A first relatively shallow control chamber 100 is formed between diaphragm surface 94 and the surface 70 of cover plate 66. A second control chamber 102 is formed between the opposite parallel surface 96 of the diaphragm and the inner 110 of the compensator body.

As best seen in FIGS. 5, 6 and 8, surface 110 of the compensator housing slopes downwardly away from the diaphragm in a generally shallow frustroconical configuration. Surface 110 intersects a short vertical wall 114 at its periphery which, in turn, extends to shoulder 92 which supports the peripheral edges of the diaphragm 90. Surface 115 peripherally supports the diaphragm above surface 110 to prevent contact between the diaphragm and the surface 110 as the diaphragm flexes in the direction of control chamber 102. Contact between the diaphragm and surface 110 could interfere with the control function. Surface 110 slopes from surface 45 to control projection 112 which will be described in detail hereafter. The configuration of the surface 10 of control chamber 102 is important and contributes to its effectiveness in minimizing air entrapment. The angle or slope of surface 110 may vary but is preferably in the range of 10° to 20°. The surface may be planar or slightly concave. The sloped or inclined surface assists in preventing air entrapment and accomodates efficient and unobstructed flow through the unit.

As seen in FIG. 7, inlet port 116 extends through the housing into chamber 102 at a location displaced from the center of the chamber. The inlet port 116 communicates with a tubular fitting 118 which extends vertically and downwardly along the rear of the compensator body as seen in FIG. 3. An outlet port 120 is formed at the approximate center of the control chamber within annularly extending projection 112. Port 120 communicates with the passage defined in fitting 122 which extends downwardly along the rear of the body of the compensator parallel to fitting 118. As best seen in FIG. 8, projection 112 has a wall 125 which diverges outwardly from port 120. A flat ramp section 126 extends around the outer periphery of the projection and is inclined downwardly intersecting surface 110. This configuration from the annulus places the effective edge of the outlet port 120 nearer to the diaphragm to provide precise control with the advantages of a deeper control chamber being retained. The walls of the projection 112 outwardly at 125 from the upper edge of the port 120 to create an entry zone or passage having a diameter greater than the internal diameter port 120. This diverging zone or entry area enhances the control precision and range of the unit. The ramp section 126 provides a smooth surface to avoid air entrapment.

Compensator 12 may be formed integrally with the controller or secured as an accessory in piggy-back fashion to the housing of flow controller 14 by attaching fitting 80 of the compensator to the inlet fitting 22 of the controller. Compensator 12 may be operatively and physically connected to the flow controller by suitable flexible tubing. Accordingly, the compensator may be easily associated with a variety of controller designs and configurations as an accessory item to provide pressure compensation.

As shown in FIGS. 1 and 2, compensator inlet 74 is connected to a source of IV fluid 130 by a suitable flexible tubing 128 in which a drip chamber 131 may be interposed. The compensator is shown as having fluid flow directed into and out of control chamber 100. Alternatively, fluid flow can be directed to chamber 100 and to the controller external of chamber 100. The important requirement is that control chamber 100 be in direct communication with the IV source so that the pressure imposed by the fluid source exists on one side of the diaphragm at chamber 100.

The outlet 26 from the flow controller, which is the metered or regulated flow, is communicated to the opposite control chamber 102 by flexible tubing 135 interconnected between fittings 26 and 118. The outlet fitting 122 from compensator control chamber 102 is connected by flexible tubing 132 to an administration needle 140 which is inserted into the patient at the venous puncture site.

In operation, the compensator 12 and controller are assembled as described above with the assembly 10 interposed at a convenient location between the IV fluid source 130 and the patient. The inlet 74 to control chamber 100 of the compensator is connected to tubing 128 leading from the IV source. It should be noted that the compensator and flow control unit may be provided as an integral set with suitable connectors convenient for this purpose. The precise location of the flow control unit and compensator is not critical except that it is customary practice to locate the device at an intermediate elevation and, since the device relies on gravity for fluid flow, the device must be positioned at a location below the level of the IV fluid. The outlet fitting 122 from the compensator control chamber 102 is connected to a tubing line 132 by a conventional connector which line leads to the patient and terminates at an administration needle 140. Once the compensator and flow control unit are connected into the delivery system, the attendant generally first will purge the system of air. This is accomplished by adjusting of the flow control unit 14 to a purge or full-flow setting. With the controller 14, dial 32 is rotated to place the inlet 22 and the outlet 26 of the flow control member in communication via flow channel 50. Full or purge flow is maintained until all air is removed from the system. The controller is then placed in an off, flow blocking position.

Thereafter, the needle is inserted in the patient at a suitable site, as for example in the hand or arm of the patient. The controller is then adjusted by the attendant to establish the desired drop rate which can be approximated from reference to the indicia 34 on the dial 32. The attendant will normally also count the drop rate by visual observation of the drip chamber to confirm the setting.

Once the flow rate has been set, using a flow controller of the type described above, the flow rate will be closely and accurately maintained were it not for variables of the delivery system. Patient movement, changes in the height of the fluid level in the IV container which changes change the head height and will affect the flow rate since the system is a gravity system. Accordingly, the pressure compensator of the present invention will automatically function to maintain a selected flow rate regardless of variation of the type mentioned above.

For example, if the level of the IV fluid drops either through the normal dissipation of the fluid or through a change in the height of the container by adjustment of the stand, this change is reflected by a reduced pressure head. Typically for most IV systems, a head of 32" of water exists between the IV solution and the patient. Seven inches of water represents average venous back pressure. However, if the head pressure is lowered, the pressure differential maintained across the opposite surfaces of the diaphragm 90 will accordingly be reduced allowing the diaphragm to move away from the outlet 120 of compensator chamber 102. This will result in a reduction of the throttling effect and compensate for the reduced head.

If the patient should extend an arm over the side of the bed lowering the location of the administration needle, the overall head pressure is increased which will result in the flexible diaphragm moving to a position closer to the outlet 120 from compensator chamber 102 resulting in increased throttling action to compensate for the increased head pressure. The shape of the chamber 102 facilitates flow and reduces the possibility of air entrapment as the shape of the control chamber does not present areas where air may lodge. The sloping surface 110 and inclined ramp 126 allow air to pass through when the system is purged. It is also important to note that the inlet port 116 communicating with chamber 102 is substantially larger than output port 112 preferably by at least a factor of two which also contributes to precise control and reduction of entrapped air. The larger inlet opening also allows faster delivery in an emergency infusion situation. Comparisons with existing devices indicate as much as 40% greater flow rates available with the present invention which could be critical in certain medical situations such as burn patients.

Tests indicate that all control functions occur at the outlet. The compensator maintains a constant differential pressure across the controller by throttling the outlet flow and, as such, operates a differential pressure regulator.

The configuration of the annular projection 112 with diverging wall 125 around the outlet port 120 renders the control function more precise and increases the operating range of the compensator. The check valve function provided by the annular projection 72 about the inlet to chamber 100 helps to keep foreign material and debris from lodging beneath the diaphragm. The diaphragm is under tension when not subjected to fluid pressure.

In order to test the effectiveness of a compensated flow control as described above, a unit in accordance with the foregoing specification was installed in a standard IV delivery system. For purposes of the test, the solution delivered was a distilled water. The system included a flexible container containing the solution connected via flexible tubing to a flow control unit and terminating at a delivery point.

TEST

Test Conditions (A) Prototype controller and compensator as described above.
(B) Standard IV pole approximately 6'.
(C) 48" from starting liquid level to needle.
(D) Needle initially 26" above floor.
(E) Controller set at rate of 100 ml/hr.
(F) Fluid contained in 500 ml. Baxter saline solution container.
(G) A non-compensated controller of the roller clamp type was used for comparison in the standard system.

| | RESULTS | |
|---|---|---|
| | % Change in Flow Rate in Standard System | % Change in Flow Rate in Compensated Unit |
| Needle Position | | |
| Moved up 24" | −50% | 0% |
| Moved up 18" | −41% | −3% |
| Moved up 10" | −20% | 0% |
| Moved down 10" | +22% | 0% |
| Moved down 20" | +33% | 0% |
| Moved down 26" | +56% | −3% |
| Liquid Level | | |
| Lowered 5" | −8% | 0% |
| Lowered 10" | −19% | 0% |
| Raised 10" | +25% | 0% |

The results demonstrate the substantial advantages with the compensator which maintain flow rates essentially constant regardless of system head fluctuations.

The present invention provides a unique, highly adaptable compensator for gravity infusion controllers. Prior to the present invention, the operating characteristics indicated above were only available with expensive and noisy electronic pumps. With the present invention, high accuracy and stable flow rates may be achieved in a manual gravity system and which also incorporates the preferred quiet operation not found with electronic pumps. A substantial cost savings to hospitals and other users result as compared with electronic devices. The unit is highly adaptable as an accessory and may be used with a variety of designs of flow controllers.

It will be obvious to those skilled in the art to make various changes, alterations and modifications to the pressure compensator described herein. To the extent such modification, changes and alterations do not depart from the spirit and scope of the appended claims, they are intended to be encompassed therein.

I claim:

1. A flow rate compensator for use with an IV administration system having a flow controller, said controller having an inlet and an outlet and an adjustable valving member for regulating fluid flow therebetween, said flow rate compensator comprising:
   (a) a housing defining an interior having opposite housing surfaces extending around the housing interior;
   (b) a flexible diaphragm having opposite first and second surfaces defined by a peripheral edge, said diaphragm extending transversely of said housing interior and having a portion of the diaphragm inward of its peripheral edge positioned between said opposite housing surfaces, said diaphragm establishing a first control chamber defined between said first diaphragm surface and said housing interior and an opposite second control chamber defined between said second diaphragm surface and said housing interior, said diaphragm having at least limited freedom of movement at its edge with respect to said opposite housing surfaces;
   (c) said first control chamber having an inlet connectable to an IV supply source;
   (d) said second control chamber having an interior surface that generally converges away from said second diaphragm surface to a projection which annularly extends around an outlet port, said second control chamber having an inlet port displaced from said outlet port and being connectable to the outlet from said controller, said outlet port from said second chamber having a cross-sectional area smaller than said inlet port to said second chamber whereby a differential in pressure existing between said second chamber and said first chamber will cause said diaphragm to move with respect to said second chamber outlet port thereby maintaining a substantially constant flow rate independent of change of pressure in the IV system.

2. The compensator of claim 1 wherein said compensator housing is injection molded from a rigid plastic.

3. The compensator of claim 1 wherein said diaphragm is silicone rubber.

4. The compensator of claim 3 wherein said diaphragm is circular.

5. The compensator of claim 1 wherein said second control chamber surface is generally concave.

6. The compensator of claim 1 wherein said second control chamber surface is generally conical.

7. The compensator of claim 1 wherein said compensator is attachable as an accessory to said controller.

8. The compensator of claim 1 wherein said second control chamber has an outlet port connectable to the inlet of said controller.

9. The compensator of claim 1 wherein said first control chamber includes a projection extending annularly about said inlet to said first control chamber.

10. The compensator of claim 1 wherein said projection at said second control chamber defines an annular entry zone to said outlet port which has a diametrical dimension greater than the outlet port.

11. The compensator of claim 10 wherein said projection has a configuration including a wall diverging outwardly from the outlet.

12. The compensator of claim 10 wherein said projection means has a first surface diverging from said outlet port and a second inclined ramp surface extending between said second control chamber interior surface and said first surface.

13. A flow rate compensated flow control device for use in an IV administration system having a source of IV fluid, said flow rate compensated flow control device comprising:
 (a) a controller having an inlet and an outlet with an adjustable valving member for regulating the fluid flow therebetween; and
 (b) a compensator including:
  (i) a housing defining an interior having opposite peripheral surfaces extending therein;
  (ii) a flexible diaphragm having a peripheral edge and opposite first and second surfaces, said diaphragm extending transversely of said housing interior and having its edge positioned between said opposite peripheral surfaces with said diaphragm being allowed at least limited freedom of movement at its peripheral edge with respect to said peripheral surfaces, said diaphragm establishing a first control chamber defined between said first diaphragm surface and said housing interior and an opposite second control chamber defined between said second diaphragm surface and said housing interior;
  (iii) said first control chamber having an inlet connectable to an IV supply source;
  (iv) said second control chamber having an interior surface that generally converges away from said second diaphragm surface to a projection which annularly extends around an outlet port, said second control chamber having an inlet port displaced from said outlet port and being connectable to the outlet from said controller, said outlet port from said second chamber having a cross sectional area smaller than said inlet port to said second chamber whereby a differential in pressure existing between said second chamber and said first chamber will cause said diaphragm to move with respect to said second chamber outlet port thereby maintaining a substantially constant flow rate independent of change of pressure in the IV system.

* * * * *